(12) United States Patent
Colman et al.

(10) Patent No.: US 8,240,187 B2
(45) Date of Patent: Aug. 14, 2012

(54) BREATH SAMPLING DEVICE AND METHOD FOR USING SAME

(75) Inventors: Joshua Lewis Colman, Jerusalem (IL); Gershon Levitsky, Jerusalem (IL)

(73) Assignee: Oridion Medical (1987) Ltd., Jerusalem (IL)

( * ) Notice: Subject to any disclaimer, the term of this patent is extended or adjusted under 35 U.S.C. 154(b) by 771 days.

(21) Appl. No.: 11/990,441

(22) PCT Filed: Aug. 16, 2006

(86) PCT No.: PCT/IL2006/000950
§ 371 (c)(1),
(2), (4) Date: Jan. 15, 2009

(87) PCT Pub. No.: WO2007/020640
PCT Pub. Date: Feb. 22, 2007

(65) Prior Publication Data
US 2009/0312662 A1     Dec. 17, 2009

Related U.S. Application Data

(60) Provisional application No. 60/709,352, filed on Aug. 16, 2005.

(51) Int. Cl.
*G01N 33/497* (2006.01)
(52) U.S. Cl. .......................................... 73/23.3
(58) Field of Classification Search .......... 73/23.3
See application file for complete search history.

(56) References Cited

U.S. PATENT DOCUMENTS

| | | | |
|---|---|---|---|
| 3,647,391 A * | 3/1972 | Keyes | ................. 422/85 |
| 4,446,869 A | 5/1984 | Knodle | |
| 5,081,871 A * | 1/1992 | Glaser | ............ 73/863.23 |
| 5,131,387 A | 7/1992 | French et al. | |
| 5,657,750 A | 8/1997 | Colman et al. | |
| 5,834,626 A * | 11/1998 | De Castro et al. | ............. 73/23.3 |
| 5,964,223 A | 10/1999 | Baran | |
| 6,422,240 B1 | 7/2002 | Levitsky | |
| 6,526,976 B1 * | 3/2003 | Baran | ............ 128/207.14 |
| 6,729,334 B1 * | 5/2004 | Baran | ............ 128/207.14 |

(Continued)

FOREIGN PATENT DOCUMENTS
WO        86/02820 A1     5/1986
(Continued)

OTHER PUBLICATIONS
PCT Search Report of PCT/IL2006/000950.
(Continued)

*Primary Examiner* — Hezron E Williams
*Assistant Examiner* — Rodney T Frank
(74) *Attorney, Agent, or Firm* — Rodney J. Fuller; Booth Udall, PLC (57) ABSTRACT

There is provided a breath sampling tube including an inner conduit, wherein at least a portion of the inner conduit is non-cylindrical and adapted to store liquids. There is also provided a breath sampling system including a gas analyzer and a breath sampling tube may include an inner conduit, wherein at least a portion of the inner conduit is non-cylindrical and adapted to store liquids. Also provided is a method of breath sampling including channeling breath through a tube having an inner conduit, wherein at least a portion of the inner conduit is non-cylindrical and adapted to store liquids.

23 Claims, 5 Drawing Sheets

U.S. PATENT DOCUMENTS

| | | |
|---|---|---|
| 6,766,817 B2 | 7/2004 | da Silva |
| 6,918,404 B2 | 7/2005 | Dias da Silva |
| 7,066,586 B2 | 6/2006 | da Silva |
| 7,220,387 B2 * | 5/2007 | Flaherty et al. .......... 422/86 |
| 7,244,398 B2 | 7/2007 | Kotary et al. |
| 7,285,255 B2 | 10/2007 | Kadlec et al. |
| 7,384,793 B2 * | 6/2008 | McCash et al. .......... 436/172 |
| RE40,618 E | 1/2009 | Nelson et al. |
| 7,472,463 B2 | 1/2009 | Gilbert et al. |
| 7,472,479 B2 | 1/2009 | Hou et al. |
| 7,472,531 B2 | 1/2009 | Fennelly |
| 7,472,584 B2 | 1/2009 | Seo et al. |
| 7,472,981 B2 | 1/2009 | Morgan et al. |
| 7,472,984 B2 | 1/2009 | Silverbrook |
| 7,473,264 B2 | 1/2009 | Allen |
| 7,473,563 B2 | 1/2009 | Cumberland et al. |
| 7,473,719 B2 | 1/2009 | Plaut et al. |
| 7,473,816 B2 | 1/2009 | Hall |
| 7,473,818 B2 | 1/2009 | Datta et al. |
| 7,475,500 B2 | 1/2009 | Covatch |
| 7,475,560 B2 | 1/2009 | Smolko et al. |
| 7,475,561 B2 | 1/2009 | Smolko et al. |
| 7,475,718 B2 | 1/2009 | Reyzin et al. |
| 7,475,744 B2 | 1/2009 | Pope |
| 7,475,825 B2 | 1/2009 | Silverbrook et al. |
| 7,475,963 B2 | 1/2009 | Hibbard et al. |
| 7,475,976 B2 | 1/2009 | Brown et al. |
| 7,476,002 B2 | 1/2009 | Wolf et al. |
| 7,476,047 B2 | 1/2009 | Brunner et al. |
| 7,476,110 B2 | 1/2009 | Lemke et al. |
| 7,476,202 B2 | 1/2009 | Raney et al. |
| 7,476,212 B2 | 1/2009 | Spearman et al. |
| 7,476,217 B2 | 1/2009 | Martin et al. |
| 7,476,533 B2 | 1/2009 | Meathrel et al. |
| 7,476,548 B2 | 1/2009 | Blatt et al. |
| 7,476,549 B2 | 1/2009 | Nahm et al. |
| 7,476,697 B2 | 1/2009 | Patacca et al. |
| 7,476,905 B2 | 1/2009 | Johnson |
| 7,476,955 B2 | 1/2009 | Street et al. |
| 7,476,965 B2 | 1/2009 | Val et al. |
| 7,477,148 B2 | 1/2009 | Lynn et al. |
| 7,477,287 B2 | 1/2009 | Silverbrook |
| 2004/0138577 A1 | 7/2004 | Kline |
| 2005/0161042 A1 | 7/2005 | Fudge |
| 2007/0292314 A1 | 12/2007 | Effenhauser et al. |
| 2008/0015531 A1 | 1/2008 | Hird et al. |

FOREIGN PATENT DOCUMENTS

| | | |
|---|---|---|
| WO | 95/31721 A1 | 11/1995 |
| WO | 2005/053542 A1 | 6/2005 |

OTHER PUBLICATIONS

Silva, Elson, "Understanding Hydrology in the Patenting System—US Pat. Application 20090312662," email dated May 6, 2010.

Supplementary European Search Report for European Patent Application No. EP06766226 dated Mar. 3, 2010 (5 sheets).

European Office Action for corresponding European patent application No. 06 766 226.2 dated May 14, 2012.

* cited by examiner

BREATH SAMPLING DEVICE AND METHOD FOR USING SAME

CROSS-REFERENCE TO RELATED APPLICATIONS

The present application is a US National Phase of PCT Application No. PCT/IL2006/000950, filed on Aug. 16, 2006, which claims the benefit under 35 U.S.C. 119(e) of US Provisional Application 60/709,352 filed Aug. 16, 2005, the entire disclosures of both of which are incorporated herein by reference.

FIELD OF THE DISCLOSURE

The present disclosure generally relates to the field of breath sampling devices.

BACKGROUND

Monitoring the concentration of exhaled carbon dioxide in order to assess the physiologic status of patients with acute respiratory problems or who are receiving mechanical ventilation, and to determine the adequacy of ventilation in anaesthetised patients, is known as Capnography. Two methods are typically employed, Mainstream Capnography and Side-stream Capnography.

The first method, known as Mainstream Capnography, consists of using an appropriate measuring sensor which is coupled and positioned on an appropriate adapter placed on the patient airway tube, connecting-the patient to the ventilation machine. This method has a disadvantage that it requires-that heavier and more cumbersome equipment be positioned in close proximity to the patient, possibly interfering with other vital medical equipment.

A second method, known as Side-stream Capnography, is based on continuous sample of breath being transferred to a remote sensor for measurement and analysis. In this method, the breath sample is transferred via an airway adapter incorporating a breath sampling port positioned in the Patient airway tubing, through a narrow diameter flexible tube, referred to as a breath sampling tube, towards the measuring sensor, known as a Capnograph, for monitoring and analysis. A liquid filtering system is normally used for controlling and handling liquids encountered in the medical environment such as may be related to patient secretions, condensed out liquids resulting from high humidity in the ventilation means, and medications and saline solutions provided to the patient during lavage, suction and nebulization procedures, and which accumulate in the Patient airway tubing.

Capnograph accuracy in monitoring and analyzing a breath sample requires that there be a continuous, smooth, laminar flow in the exhaled gases when moved from the patient to the measuring sensor, such that the effect on the exhaled gas waveform is maintained to a minimum. In a typical side-stream system, a standard airway adapter for breath sampling in a Patient airway tubing-would have as a basic design a tube of approximately 15 mm internal diameter and some 60 mm long with appropriate medical standard conical fittings at either end (to serially connect to the Patient airway tubing). Mid way along the tube would be attached a small bore sampling tube, 1 mm-2 mm internal diameter, referred to as a sampling port, perpendicular-to the axis of the gas flow in the Patient airway tubing, and reaching close to the center-of the tube on one side and on the other side exiting the tube wall to be connected to the breath sampling tube. The Capnograph will then continuously provide a suction effect, typically by means of a diaphragm pump, which is measured as a pressure drop, at the sampling port in order to receive a continuous sample of gas for analysis.

Filtering systems utilized in Side-stream Capnography are designed to attempt to minimize the possibility that liquids can collect in the breath sampling tube and reach the sensitive components of the Capnograph and/or block the breath sampling tube, consequently interfering with the continuous monitoring of the subjects breath. Several methods have been developed for this purpose, some designed to prevent liquids from entering the breath sampling tube, and some designed to remove the liquids once inside the breath sampling tube. These may include:

a. A specially designed airway adapter fitted on the Patient airway tubing and to which is connected the breath sampling tube.
b. A Nafion (or similar) tube, which may form part of the breath sampling tube, for reducing humidity and consequently reducing the possibility for condensed out liquids to collect.
c. A reservoir in the breath sampling tube for collecting liquids accumulated in the breath sampling tube and removing the liquids from the gas flow path.
d. A hydrophobic membrane to prevent any liquid managing to pass the above elements and which will cause damage to the Capnograph.

One of the major obstacles when designing a filter system is the necessity to prevent any liquids from blocking the breath sampling path or from reaching the measurement sensor while providing continuous, smooth, undisturbed sampling of the patients breath (exhaled waveform). This waveform related requirement places a series of constraints on the design of the filter. As described in U.S. Pat. No. 5,657,750, distortion to smooth unimpaired gas flow in the prior art fluid filters are caused by three major factors:

a. By the materials of the filtering device itself, including the porous portions of the filtering membrane and porous portions of the wall thereof, to an extent proportional to their thickness;
b. By the shape or configuration of the filter body itself, preventing abrupt changes in the gas passageway between inlet and outlet thereof, and
c. By the overall size of the volume or space of the passageway for the gas flow from the inlet to the outlet of the filter.

A major problem with currently known filter systems is that typically, the volume of the traps or reservoirs is small, 100-300 micro-liter, so as to have minimum influence on the waveform of the exhaled gas. Hence small quantities of liquid can result in quick overfilling of the reservoir which can then result in blockage of the breath sampling tube.

Many techniques have been used in the attempt to filter out liquids from the exhaled gas without affecting the waveform in the breath sampling tube. Such techniques have included absorbents for wicking out condensate out of the gas, centrifugal filters, dessicants, hydrophobic membranes for filtering gases, and hydrophilic membranes for filtering liquids, all having their advantages and disadvantages. Nevertheless, none are able to remove all the liquids in the breath sampling tube without the intervention of a hydrophobic filter, which may have an effect on the waveform of the exhaled gas. A hydrophobic filter is dictated, since after any reservoir fills, the liquids may overflow and reach-the gas analyzer, hence a hydrophobic filter is used as a fuse together with the liquid reservoir. However, when placing this fuse in close proximity to the liquid reservoir/collector, as typically done, the entry of liquid may often be too fast for the liquid reservoir to absorb the entire volume and part of the liquid may pass the reservoir and reaches the fuse far before the reservoir is full. The design of the reservoir may thus interfere with the waveform, specifically, since the gas sample flows and mixes in the reservoir.

There is therefore a need for a filter system which includes a liquid storage element, more specifically a reservoir, which can be added between the airway adapter and the measurement sensor, and will serve to temporarily store all liquids in such a way that they are dried up over a period of time or dispensed off in small quantities (droplets) along the breath sampling tube such that they also are dried up over time, and which will not disturb the waveform of the exhaled gas.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other advantages or improvements.

In one embodiment there is provided a breath sampling tube including an inner conduit, wherein at least a portion of the inner conduit is non-cylindrical and adapted to store liquids. In another embodiment, there is provided a breath sampling system including a gas analyzer and a breath sampling tube may include an inner conduit, wherein at least a portion of the inner conduit is non-cylindrical and adapted to store liquids. In yet another embodiment, there is provided a method of breath sampling including channeling breath through a tube having an inner conduit, wherein at least a portion of the inner conduit is non-cylindrical and adapted to store liquids.

There is further provided, according to additional embodiments, a self-drying liquid reservoir for a breath sampling tube comprising a housing having a diameter larger than the diameter of the sampling tube; and a wick material essentially within the housing adapted to retain liquid, wherein the reservoir is adapted to permit gas flow through the housing. In another embodiment, there is provided a breath sampling system including a gas analyzer and a self-drying liquid reservoir for a breath sampling tube comprising a housing having a diameter larger than the diameter of the sampling tube; and a wick material essentially within the housing adapted to retain liquid, wherein the reservoir is adapted to permit gas flow through the housing. In another embodiment, there is provided a method of breath sampling comprising channeling breath through a self-drying liquid reservoir for a breath sampling tube comprising a housing having a diameter larger than the diameter of the sampling tube and a wick material essentially within the housing adapted to retain liquid, wherein the reservoir is adapted to permit gas flow through the housing.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in the referenced figures. It is intended that the embodiments and figures disclosed herein be considered illustrative, rather than restrictive. The disclosure, however, both as to organization and method of operation, together with objects, features, and advantages thereof, may best be understood by reference to the following detailed description when read with the accompanying figures, in which.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

In the following detailed description of the preferred embodiment numerous specific details have been set forth in order to provide a thorough understanding of the invention. However, it will be understood by those skilled in the art that the preferred embodiment described herein may be practiced without these details and therefore it is not intended to limit the invention to the precise form disclosed.

The numbering system employed herein is based on assigning every part or element a three digit number. The first digit relates the part or element to the figure in which it is called out. The other two digits are the specific identifier of the part or element. It will be repeatedly encountered throughout this detailed description that similar, or even the same, parts or elements will appear in different figures. These parts or elements may be identified through the same specific identifier, that is, the last two digits in the assigned part number are the same.

In one embodiment there is provided a breath sampling tube including an inner conduit, wherein at least a portion of the inner conduit is non-cylindrical and adapted to store liquids. In another embodiment, there is provided a breath sampling system including a gas analyzer and a breath sampling tube may include an inner conduit, wherein at least a portion of the inner conduit is non-cylindrical and adapted to store liquids. In yet another embodiment, there is provided a method of breath sampling including channeling breath through a tube having an inner conduit, wherein at least a portion of the inner conduit is non-cylindrical and adapted to store liquids.

It is noted that the breath sampling tube having an inner conduit, at least a portion of which is non-cylindrical, may be integrally formed with a commonly used breath sampling tube or a separate element (and/or an "add-on") which may be attached to a breath sampling tube, for examples by adaptor(s) and or connector(s).

The inner conduit (which may also be referred to herein as conduit) may further be adapted to permit gas flow out of the conduit wherein the gas is essentially free of liquids. The inner conduit may be adapted to store liquids along the surface of the conduit and to permit gas flow along the central portion of the conduit. The inner conduit may be adapted to permit gas flow along the surface of the conduit and to store liquids along the central portion of the conduit. The walls of the inner conduit may include a hydrophilic material. The walls of the inner conduit may include a hydrophobic material. The walls of the inner conduit comprises a hydrophilic material and another portion of the walls of the inner conduit comprises a hydrophobic material. The inner conduit may include a first lumen and a second lumen connected to each other along the inner conduit. The diameter of the first lumen is larger than the diameter of the second lumen. The cross section of the inner conduit may be essentially similar to the digit 8. The inner conduit may include a hydrophobic material. The inner conduit may be adapted to collect liquids in the first lumen. The inner conduit may be adapted to permit gas flow in the second lumen. The surrounding surface of the first lumen may be essentially more hydrophilic than the surrounding surface of the second lumen. The lumen in which liquid may be accumulated may be referred to as a tube collector, which may be a part of the conduit. The inner conduit may be adapted to collect liquids in the first lumen. The inner conduit may be adapted to permit gas flow in the second lumen.

The cross section of the inner conduit may essentially be non-circular. The cross section of the inner conduit is essentially similar to an n-petal flower, wherein n is an integer having the value of between 2-100, for example 2-10, 4-20, 5-50. The cross section of the inner conduit may essentially be similar to an n-point star, wherein n is an integer having the value of between 2-100, for example 2-10, 4-20, 5-50.

The inner conduit may be adapted to permit self-drying of the liquids. Self drying may be achieved by the flow of the gas within the conduit.

There is further provided, according to additional embodiments, a self-drying liquid reservoir for a breath sampling tube comprising a housing having a diameter larger than the diameter of the sampling tube; and a wick material essentially within the housing adapted to retain liquid, wherein the reservoir is adapted to permit gas flow through the housing. In another embodiment, there is provided a breath sampling system including a gas analyzer a self-drying liquid reservoir for a breath sampling tube comprising a housing having a diameter larger than the diameter of the sampling tube; and a wick material essentially within the housing adapted to retain liquid, wherein the reservoir is adapted to permit gas flow through the housing.

In another embodiment, there is provided In another embodiment, there is provided a method of breath sampling comprising channeling breath through a self-drying liquid reservoir for a breath sampling tube comprising a housing having a diameter larger than the diameter of the sampling tube and a wick material essentially within the housing adapted to retain liquid, wherein the reservoir is adapted to permit gas flow through the housing. The wick may include a porous material.

The liquid reservoir may be located in close proximity to the moisture reduction system. The term "close proximity" may refer to 50 cm (centimeters) or less, for example, 30, 20, 15, 10, 5, 1 cm or less, 0.5 cm or less.

The liquid reservoir may be located in proximity to the airway adaptor or to any respiratory output device (such as a mask, oral and/or nasal breath collectors, endotracheal tube intubation tube and the like). The term "proximity" may refer to 100 cm (centimeters) or less, for example, 50, 20, 15, 10 or 5.

The liquid reservoir may be may be located within a certain distance from a gas analyzer. The term "certain distance" may refer to a distance larger than 10 cm, for example larger than 20 cm, 30 cm, 40 cm or 50 cm, 70 cm.

Figure 1:
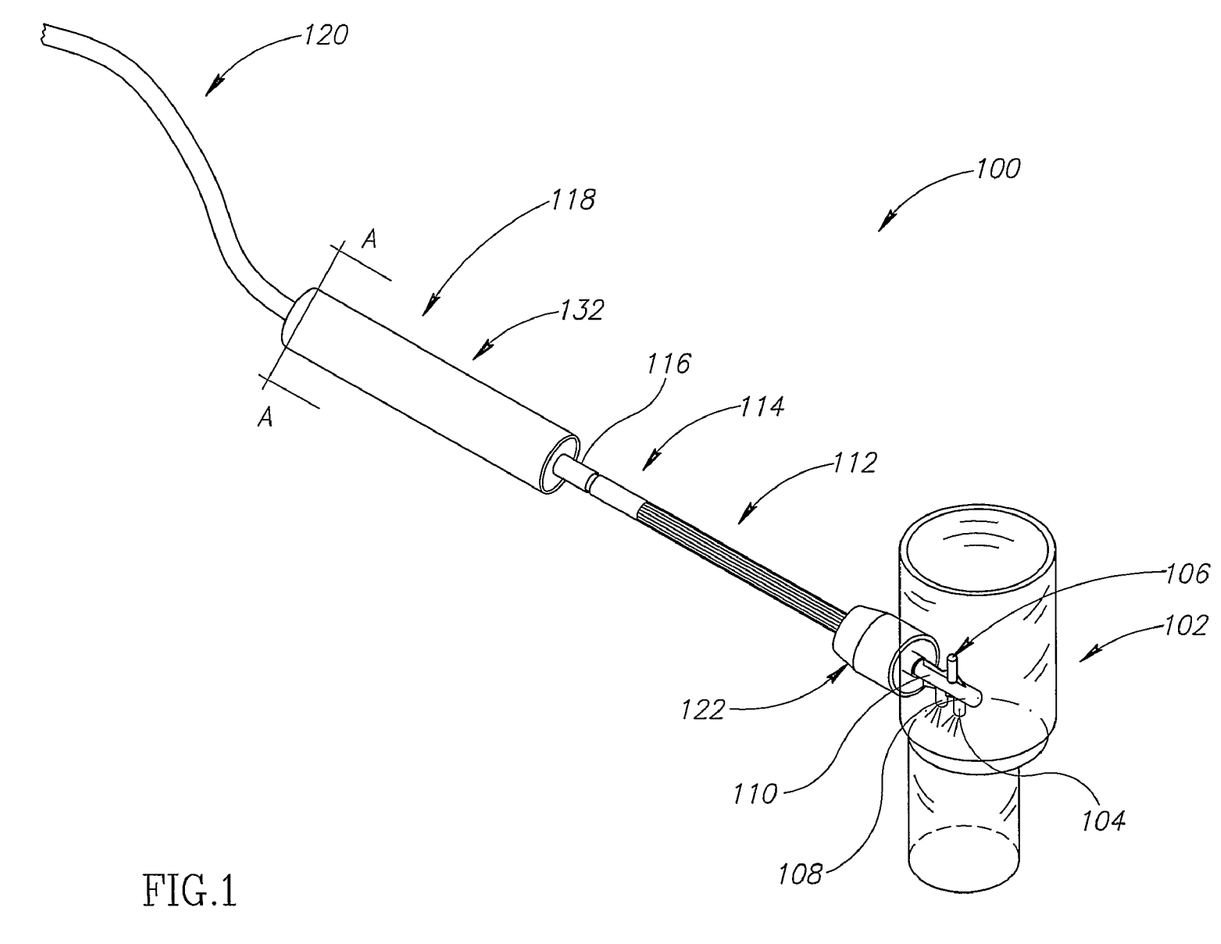
FIG. 1 shows an Assembly Drawing of a part of a Sidestream Breath Sampling System with a Liquid Reservoir.

Reference is now made to FIG. 1 which shows an assembly drawing of part of a side-stream breath sampling system which connects to the patient airway tubing. The sampling system (100) is adapted for the accurate sampling and analysis of exhaled breath by controlling and reducing the influx of moisture and liquid from exhaled breath and from possible extraneous sources.

Exhaled breath sample collection is done through the airway adapter (102), which may be essentially a tube with connector fittings at each end which may be adapted to a patient airway tubing and to which may be fitted at least one sampling port (110) as shown. The sampling port (110) includes at least one sampling inlet (104) through which the exhaled breath sample is collected and passed into the sampling system (100) through the sampling port (110). In the sampling port (110) shown, included are a second sampling inlet (106) and a third sampling inlet (108), although a larger number may also be included. The sampling port (110) and the sampling inlets (104, 106, 108) may be configured in the airway adapter (102) in varying numbers, shapes and lengths, as well as in different positions within the airway adapter (102).

The exhaled breath sample connected in the airway adaptor (102) by the sampling inlets (104, 106, 108) is passed through the sampling port (110) into a moisture reduction system (112), hereinafter referred to as MRS. The MRS (112) may be a specially designed tube, which may be of variable length and diameter, adapted to reduce moisture entering the sampling system (100) in order to limit possible incorrect monitoring and analysis of the of the exhaled breath sample as well as limit possible damage to the monitoring equipment (not shown) due to moisture. The MRS (112) may include any drying mechanism and/or material, essentially impermeable to gas, that is capable of reducing moisture level, for example Nafion®, or may include filters such as micro-porous filters or molecular sieves (material containing tiny pores of a precise and uniform size that may be used to absorb moisture.

The MRS (112) may be fitted at one end with a connector (122) which is adapted to firmly secure the MRS (112) in place with the sampling port (110). The connector (122) is designed to limit interference with the flow of the exhaled breath sample by sources external to the sampling system (100) and to restrict exhaled breath sample leakage. At the other end the MRS (112) may be fitted with a tube connector (114), which may be, for example, a molded-on connector, adapted to connect the MRS (112) with a short inlet tube (116). The tube connector (114), similar to the connector (122), is also designed to limit interference with the flow of the exhaled breath sample by sources external to the sampling system (100) and to limit escape of the exhaled breath sample.

A primary element for liquid reduction and removal in the sampling system (100) is a liquid reservoir (118). The liquid reservoir (118) may be serially connected to the MRS (112), as shown, through the inlet tube (116), a conductor with a narrow bore of a diameter so as to not affect the waveform of the exhaled breath sample, for example 1 mm to 2 mm. The exhaled breath sample passes from the MRS (112) after drying into the inlet tube (116) from where it passes into the liquid reservoir (118). The inlet tube (116) may be of a circular cross-section, but may essentially be of any shape. The inlet tube (116) may be made either from a plastic or non-plastic material, although it is generally made from flexible PVC for ease in handling and cost considerations.

The liquid reservoir (118) may include a housing (132) which may be cylindrical in shape as shown, although it may have other shapes such as rectangular, elliptical, and more, containing a wick material (not shown), which may be, for example, made of a hydrophilic material. The wick material may be adapted-for the absorption of liquids while permitting the gas to flow through. The hydrophilic material may be preferably made in a fiber form pressed into a rod shape, with pore sizes of 5 to 70 microns, preferably 20 to 50 microns, and may have a high pore to material ratio of 30% to 95% pore volume, preferably 50% to 80% pore volume. A preferable material for this purpose may be cellulose acetate. The pressure drop across the ends of the wick material should not be too high, less than 30 mbar, for example 15 mbar, when a gas flow of 50 ml/min is passed through the wick material.

The wick material may have a diameter between 1 mm to 4 mm, preferably in the 2.5 mm to 3 mm range. The length may be between 10 mm to 50 mm long, although the final dimensions should be chosen so that on one hand it may have a volume large enough to contain at least one volume of liquid that could enter the inlet tube (116). In this way, each time liquids enter the liquid reservoir (118) then the entire volume is not filled, and the gas can continue to flow with minor changes in pressure drop. Since the liquid within the liquid reservoir (118) is spread out, the continuous flow of MRS (112) dried exhaled breath sample, passing through can assist to dry the volume of the liquid that entered the liquid reservoir (118).

The dry exhaled breath sample passes from the liquid reservoir (118) into the outlet tube (120), which is essentially liquid-free due to the liquid filtering effect of the liquid reservoir (118), and to the measurement sensor (not shown) where the sample is monitored and analyzed. The outlet tube (120) may be of similar characteristics as the inlet tube (116), a conductor with a narrow bore of a diameter so as to not affect the waveform of the exhaled-breath sample, for example 1 mm to 2 mm and may be several meters long, for example 2 to 6 meters. The outlet tube (120) may be of a circular cross-section, but may essentially be of any shape. The outlet tube (120) may be made either from a plastic or non-plastic material, although it is generally made from flexible PVC for ease in handling and cost considerations.

Figure 2:
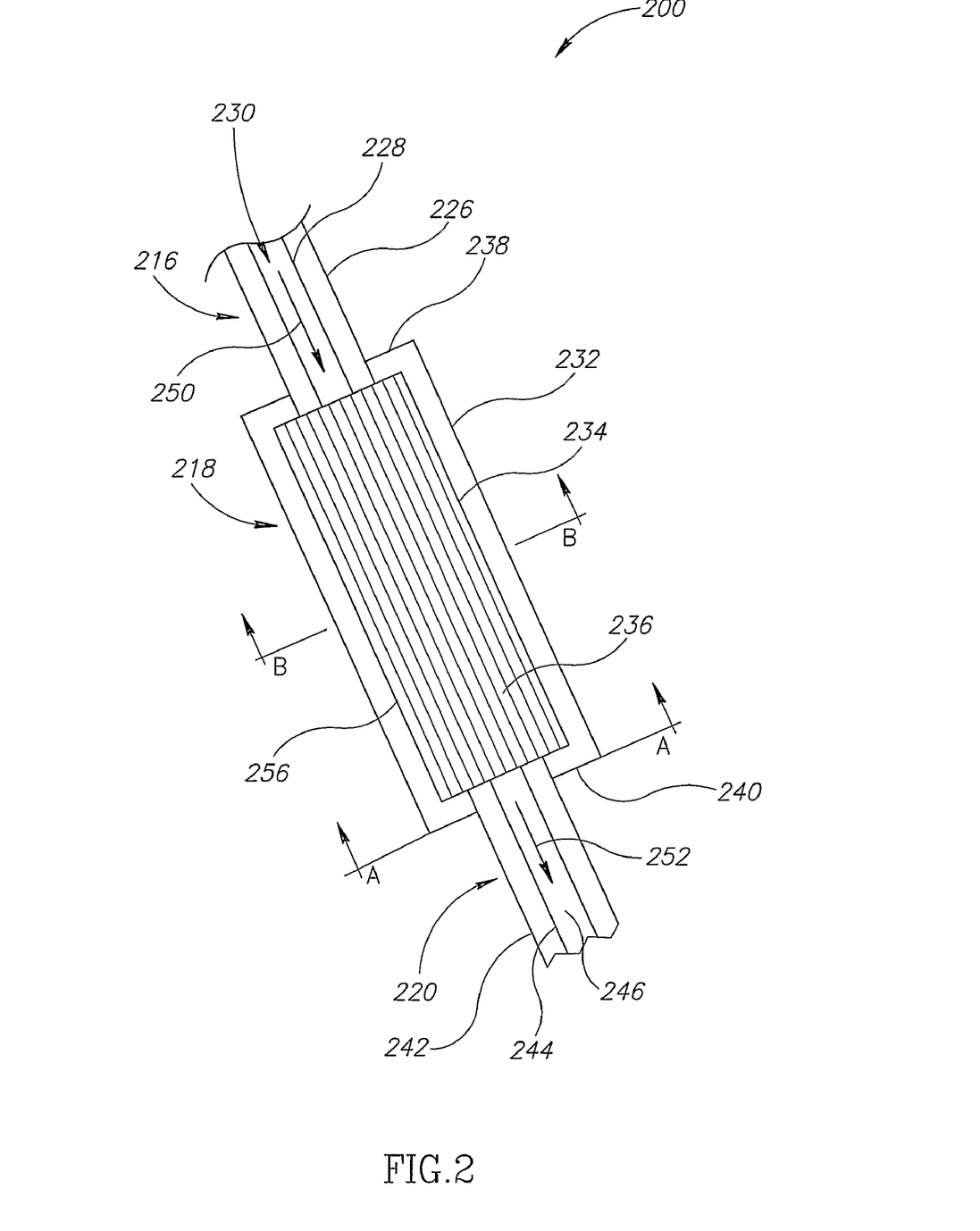
FIG. 2 shows a Longitudinal Cross-Section View A-A of a Liquid Reservoir.

Reference is made to FIG. 2 which shows a longitudinal cross-sectional view A-A of a preferred embodiment of the liquid reservoir (218) as indicated in FIG. 1. The liquid reservoir (218) includes a housing (232) which may be, for example cylindrical in shape, although the shape of the present embodiment is not limited to having a particular type of cross-section.

The housing (232) extends at one end to the inlet end (238), through which the inlet tube (216) connects to the liquid reservoir (218), and extends at the other end to the outlet end (240), through which the outlet tube (220) connects to the liquid reservoir (218). During normal operation, fluids, which may include the exhaled breath sample and other liquids common to a medical environment, flow into the inlet end (238) of the liquid reservoir (218) through the inlet tube (216), as shown by the direction of fluid flow (250), flows through a wick material (236) where the liquids may be absorbed or filtered, and on to exit through the outlet end (240) of the liquid reservoir (218) into the outlet tube (220), as shown by the direction of the dried gas (252).

The housing (232) includes an inner wall (234) which defines the boundary of a wick material (236), which includes a hydrophilic material (236), inside the liquid reservoir (218). The hydrophilic material (236) may be preferably-made in a fiber form with pore sizes of 5 to 70 microns, preferably 20 to 50 microns, and may have a high pore to material ratio of 30% to 95% pore volume, preferably 50% to 80% pore volume. A preferable material for this purpose may be cellulose acetate. The border of the wick material (236) with the inner wall (234) of the housing (232) is the wick wall (256) The wick wall (256) is essentially attached to the inner wall (234) so as to form an impermeable border which is practically fluid-tight, thereby restricting possible influx of fluids from outside the sampling system (200).

Fluid flow inside the liquid reservoir (218) is directed from the inlet end (238) to the outlet end (240) along the wick material (236), wherein the liquids are absorbed by the hydrophilic material (236) while the gas may flow through with minimum perturbation. The liquids are then stored within the hydrophilic material (236) and subsequently dried by the exhaled breath sample previously dried by the MRS (212).

The wick material as referred to herein may include a conduit (such as the conduit described herein) which may extend from the inlet end to the outlet end, through which fluid may flow. At least a portion of the inner conduit may be non-cylindrical (for example as described herein).

The inlet tube (216) may be a short flexible tube which may include an inlet bore (230) of diameter 0.5 mm-4 mm, preferably 1 mm-2 mm, through which the exhaled breath sample may flow without waveform interference. The inlet tube (216) includes an inlet inner wall (228), hereinafter referred to as IIW, which forms the boundary of the inlet bore (230) and an inlet outer wall (226), hereinafter referred to as IOW, forming the external surface of the inlet tube (216). The inlet tube (216) shown is of a circular cross-section, but may essentially be of any shape. The inlet tube (216) may be made either from a plastic or non-plastic material, although it is generally made from flexible PVC for ease in handling and cost considerations, as shown.

The outlet tube (220) may be a flexible tube which may include an outlet bore (246) of diameter 0.5 mm-4 mm, preferably 1 mm-2 mm, through which the exhaled breath sample may flow without waveform interference after exiting the liquid reservoir (218). The length of the outlet tube (220) may extend for several meters, for example 2 to 6 meters. The outlet tube (220) includes an outlet inner wall (244), hereinafter referred to as OIW, which forms the boundary of the outlet bore (246) and an outlet outer wall (242), hereinafter referred to OOW forming the external surface of the outlet tube (220). The outlet tube (220) shown is of a circular cross-section, but may essentially be of any shape. The outlet tube (220) may be made either from a plastic or non-plastic material, although it is generally made from flexible PVC for ease in handling and cost considerations, as shown.

Referring to FIG. 1 the following is a description of the operation of the side-stream sampling system (100) described by this preferred embodiment. A patient is connected to a breathing apparatus or to some other ventilation means through a breathing tube or airway tube which is also known as a patient airway tubing and to which is adapted an airway adapter (102). Samples of the CO2 exhaled by the patient, which may sporadically combine together with other liquid secretions such as blood, mucus, water, medications, and the like, are sucked into the sampling inlets (104, 106, 108) in the airway adapter (102) and into the sampling port (110), also forming part of the airway adapter (102), as a result of the suction action-of the pump-in the measurement sensor (not shown). These exhaled breath samples combine the exhaled CO2 with liquids with a relatively high viscosity so that there is a natural tendency for clogging in many parts of the sampling system (100) due to the small diameters employed in the parts for accurate measurement purposes. The sampling inserts (102, 104, 106) work in parallel such that only one is required for proper sampling should the other two cease to function due to clogging.

The combination of the CO2 and the liquid secretions pass from the sampling port (110) into the MRS (112) where moisture is extracted from the exhaled breath samples. The MRS (112) is placed as close as possible to the airway adaptor (102) so as to immediately try to counteract the effects of the liquids in the exhaled breath samples which, as previously mentioned, may contribute to clogging in the sampling system (100). Although the MRS (112) may be able to extract a portion of the moisture/humidity, significant amounts of moisture/humidity and liquids may remain in the exhaled breath samples which may hamper the accurate monitoring and analysis of the samples by the measurement sensor in addition to possibly blocking the path of the flow of the samples in the sampling system (100).

The exhaled breath samples move through the short inlet tube (116) into the liquid reservoir (118), which may be positioned in close proximity to the MRS (112). The liquid reservoir (118) may serve as a filter to trap the remaining moisture and liquids in the samples. Inside the liquid reservoir (118) the samples encounter a hydrophilic material which serves to separate the liquids from the exhaled CO2 samples. The liquids remain trapped inside the liquid reservoir while the dried CO2 samples continue through the outlet tube (120) to the measurement sensor. The design of the liquid reservoir (118) must allow for sufficient liquid storage so as to restrict overfilling while permitting slow drying of the liquids by the constant passage of dry CO2 samples. Additionally, the design of the liquid reservoir (118) must ensure minimum interference with the waveform of the exhaled breath samples.

Figure 3:
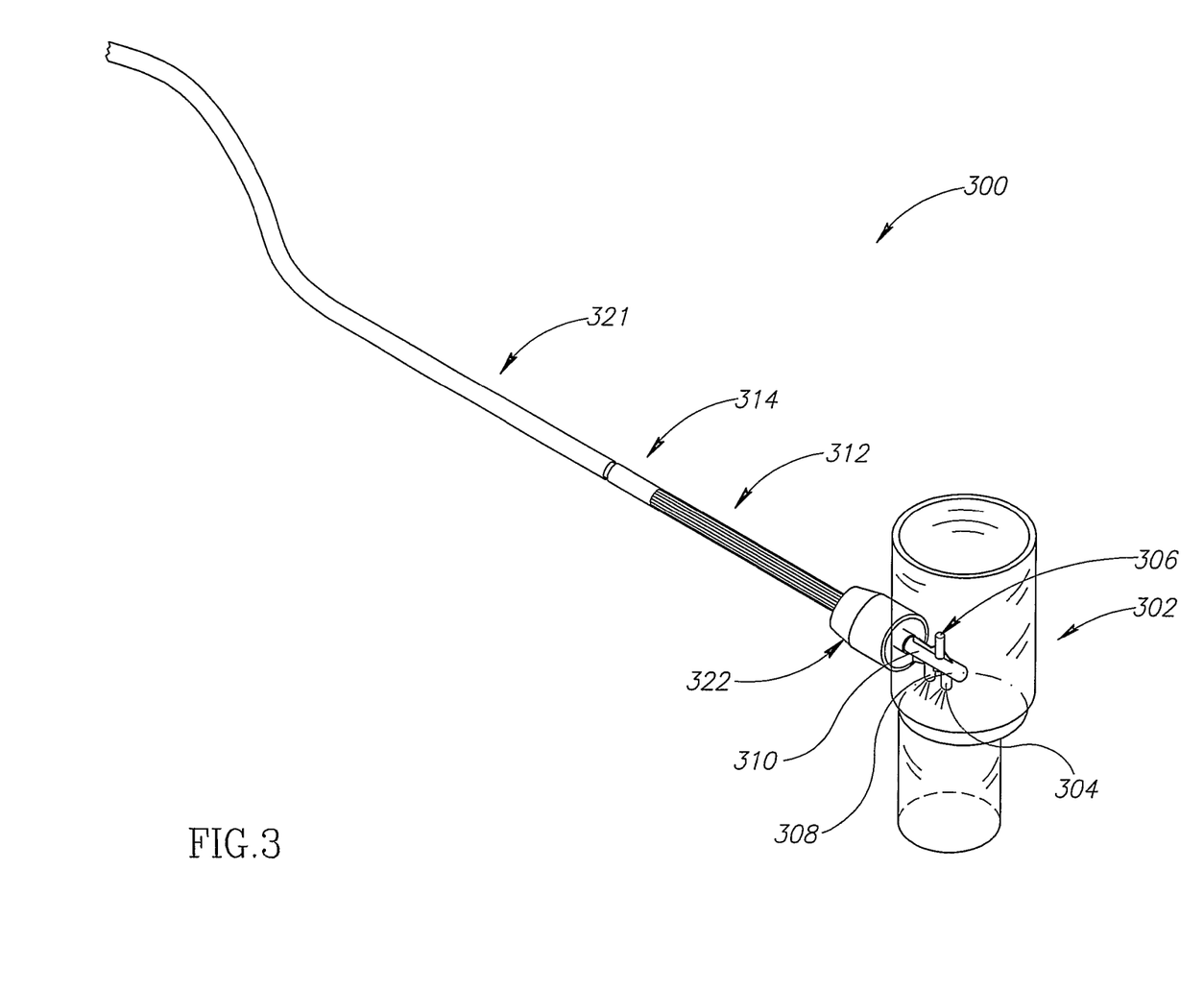
FIG. 3 shows an Assembly Drawing of a part of a Sidestream Breath Sampling System with a Liquid Removal Sampling Line.

Reference is made to FIG. 3 which shows an alternative embodiment to the sides-stream sampling system (300). The sampling system (300) is adapted for the accurate sampling and analysis of exhaled breath by controlling and reducing the influx of moisture and liquids from exhaled breath and from possible extraneous sources.

Exhaled breath sample collection is done through the airway adapter (302), which may be essentially a tube with connector fittings at each end which may be adapted to a patient airway tubing and to which may be fitted at least one sampling port (310) as shown. The sampling port (310) includes at least one sampling inlet (304) through which the exhaled and inhaled breath sample is collected and passed into the sampling system (300) through the sampling port (310). In the sampling port (310) shown, included are a second sampling inlet (306) and a third sampling inlet (308), although a larger number may also be included. The sampling port (310) and the sampling inlets (304, 306, 308) may be configured in the airway adapter (302) in varying numbers, shapes and lengths, as well as in different positions within the airway adapter (302).

The exhaled breath sample collected in the airway adaptor (302) by the sampling inlets (304, 306, 308) may be passed through the sampling port (310) into a moisture reduction system (312), hereinafter referred to as MRS. The MRS (312) may be a specially designed tube, which may be of variable length and diameter, adapted to reduce moisture/humidity entering the sampling system (300) in order to limit possible incorrect monitoring and analysis of the of the exhaled breath sample as well as limit possible damage to the monitoring equipment (not shown) due to moisture and/or condenced liquid. The MRS (312) may include any drying mechanism and/or material, essentially impermeable to gas, that is capable of reducing moisture level, for example Nafion®, or may include filters such as micro-porous filters or molecular sieves (material containing tiny pores of a precise and uniform size that may be used to absorb moisture.

The MRS (312) may be fitted at one end with a connector (322) which is adapted to firmly secure the MRS (312) in place with the sampling port (310). The connector (322) is designed to limit interference with the flow of the exhaled breath sample by sources external to the sampling system (300) and to restrict escape of the exhaled breath sample. At the other end the MRS (312) may be fitted with a tube connector (314), which may be, for example, a molded-on connector, adapted to connect the MRS (312) with a sampling tube (321). The tube connector (314), similar to the connector (322), is also designed to limit interference with the flow of the exhaled breath sample by sources external to the sampling system (300) and to limit escape of the exhaled breath sample.

A primary element for liquid reduction and removal in the sampling system (300) is the sampling tube (321), also used as the conduit for the exhaled breath sample to the measurement sensor (not shown). The sampling tube (321) may be connected in series with the MRS (312), as shown, and is adapted to collect liquids in the exhaled breath sample without interfering with the waveform of the sample. The exhaled breath sample passes from the MRS (312) after drying, into the sampling tube (321), from where it is conducted on to the measurement sensor. The sampling tube (321) may have a cross-section which may essentially be of any shape which facilitates liquid collection and uninterfered gas transport. The sampling tube may be made either from a plastic or non-plastic material, its interior including a hydrophilic and/or hydrophobic material along a portion of the length, which can also be the whole length, of the sampling tube (321). The liquids entering the line may then spread out along the length of the hydrophilic and/or hydrophobic material, thereby limiting the probability of clogging and permitting natural drying of the liquids.

The sampling tube (321) made be of hydrophilic and/or hydrophobic material, for example Nafion for a hydrophilic tube and Teflon or polyacetal for a hydrophobic tube. Alternatively, the tube made not be of a hydrophilic nor hydrophobic material, for example PVC, and it may have a hydrophilic and/or hydrophobic coating (not shown) installed along the inside wall (not shown) of the sampling tube (321).

Referring to FIG. 3 the following is a description of the operation of the side-stream sampling system (300) described as an alternative embodiment. A patient is connected to a breathing apparatus or to some other ventilation means through a breathing tube or patient airway tube to which is adapted an airway adapter (302). Samples of the CO2 exhaled by the patient, which may sporadically combine together with other liquid secretions such as blood, mucus, water, medications, and the like, are sucked into the sampling inlets (304, 306, 308) in the airway adapter (302) and into the sampling port (310), also forming part of the airway adapter (302) as a result of the suction action of the pump in the measurement sensor (not shown). These exhaled breath samples then combine the exhaled CO2 with liquids with a relatively high viscosity so that there is a natural tendency for clogging in many parts of the sampling system (300) due to the small diameters employed in the parts for accurate measurement purposes. The sampling inserts (302, 304, 306) work in parallel such that only one is required for proper sampling should the other two cease to function due to clogging.

The combination of the $CO_2$ and the liquid secretions pass from the sampling port (310) into the MRS (312) where moisture is extracted from the exhaled breath samples. The MRS (412) is placed as close as possible to the airway adaptor (302) so as to immediately try to counteract the effects of the liquids in the exhaled breath samples which, as previously mentioned, may contribute to clogging in the sampling system (300). Although the MRS (312) is able to extract a good portion of the moisture and liquids, significant amounts may remain in the exhaled breath samples which may hamper the accurate monitoring and analysis of the samples by the measurement sensor in addition to possibly blocking the path of the flow of the samples in the sampling system (300).

The exhaled breath samples move into the sampling tube (321) where it encounters a hydrophilic material, which may also be a hydrophobic material or a combination of a hydrophilic and hydrophobic material, which serves to separate the liquids from the exhaled CO2 samples. The liquids remain trapped inside a tube collector (not shown) in the sampling tube (321) while the dried CO2 samples continue through to the measurement sensor. The design of sampling tube (321) may allow for sufficient liquid storage so as to restrict clogging and possible interference with the waveform of the exhaled breath samples, while permitting slow drying of the liquids by the constant passage of the dry CO2 samples. It is noted that the tube collector may be an integral part of the sampling tube itself, having a shape that provides the liquid collecting features.

Figure 4A:
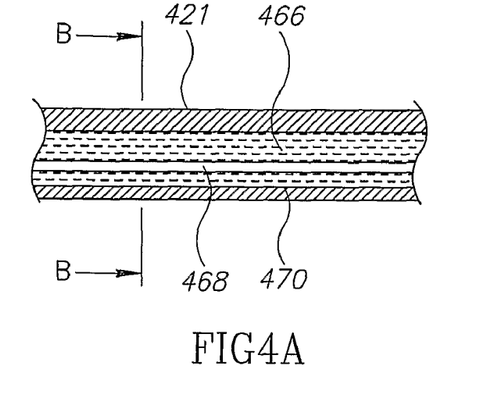
FIG. 4a shows a Longitudinal Cross-Sectional View of a Portion of the Sampling Tube in a First Embodiment of the Sampling Tube.
Figure 4B:
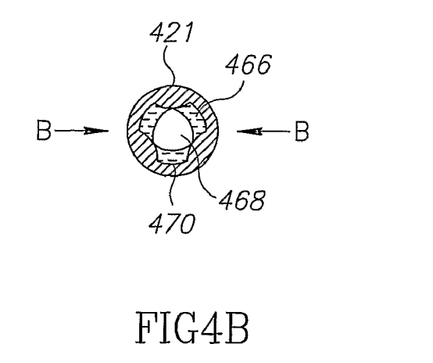
FIG. 4b shows a Transversal Cross-Sectional View B-B of a Portion of the Sampling Tube in a First Embodiment of the Sampling Tube.

Reference is made to FIG. 4a which shows a longitudinal cross-sectional view of a portion of the sampling tube (421) and FIG. 4b which show a transversal cross-sectional view B-B of a portion of the sampling tube (421). The sampling tube (421) may include hydrophilic material, for example, glass or Nafion for a hydrophilic tube and Teflon or polyacetal for a hydrophobic tube. Alternatively, the tube may include a hydrophilic coating (not shown) installed along the conduit wall (470) of the sampling tube (421).

The sampling tube (421) which may include hydrophilic material, and may include a conduit (468) essentially shaped in the form of a "three petal flower", a center duct from which branch out three additional ducts. The liquid will accumulate along the conduit wall (470) of the sampling tube (421) due the hydrophilic characteristics of the conduit wall (470). This configuration offers increased liquid collection (466) within the sampling tube (421) compared to a circular cross-sectional configuration, as the contact surface area between the liquid and the conduit wall (470) is increased and the liquids are trapped against the conduit wall (470). The central section of the conduit (468) is then left free for the gas to flow along.

Figure 5A:
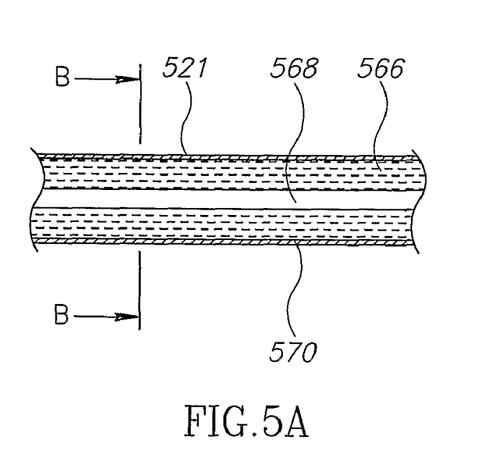
FIG. 5a shows a Longitudinal Cross-Sectional View of a Portion of the Sampling Tube in an Alternate Embodiment of the Sampling Tube.
Figure 5B:
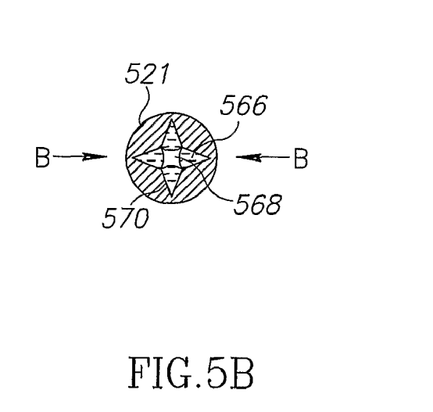
FIG. 5b shows a Transversal Cross-Sectional View B-B of a Portion of the Sampling Tube in an Alternate Embodiment of the Sampling-Tube.

Reference is made to FIG. 5a which shows a longitudinal cross-sectional view of a portion of the sampling tube (521) and FIG. 5b which show a transversal cross-sectional view B-B of a portion of the sampling-tube (521). The sampling-tube (521) may include hydrophilic material, for example, glass or Nafion for a hydrophilic tube and Teflon or polyacetal for a hydrophobic tube. Alternatively, the tube may include a hydrophilic coating (not shown) installed along the conduit wall (570) of the sampling tube (521).

The sampling tube (521) which may include hydrophilic material, and may include a conduit (568) essentially shaped in the form of a "four point star", a center duct from which branch out four sections. The liquid will accumulate along the conduit wall (570) of the sampling tube (521) due the hydrophilic characteristics of the conduit wall (570). This configuration offers increased liquid collection (566) within the sampling tube (521) compared to a circular cross-sectional configuration, as the contact surface area between the liquid and the conduit wall (570) is increased and the liquids are trapped against the conduit wall (570). The central section of the conduit (568) is then left free for the gas to flow along.

Figure 6A:
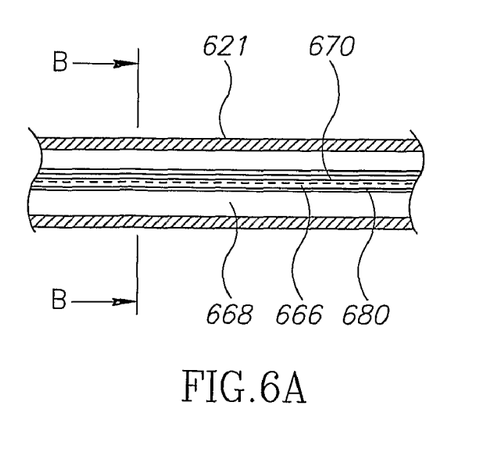
FIGS. 6a and 7a show a Longitudinal Cross-Sectional View of a Portion of the Sampling Tube in an Alternate Embodiment of the Sampling Tube.
Figure 6B:
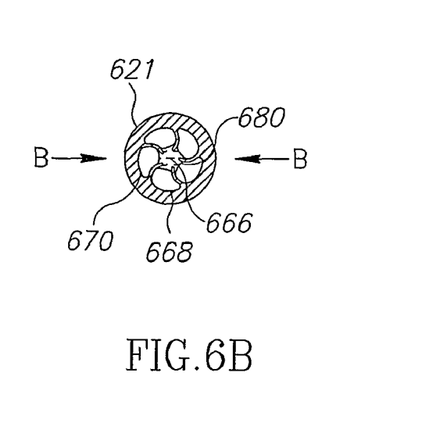
FIGS. 6b and 7b show a Transversal Cross-Sectional View B-B of a Portion of the Sampling Tube in an Alternate Embodiment of the Sampling Tube.
Figure 7A:
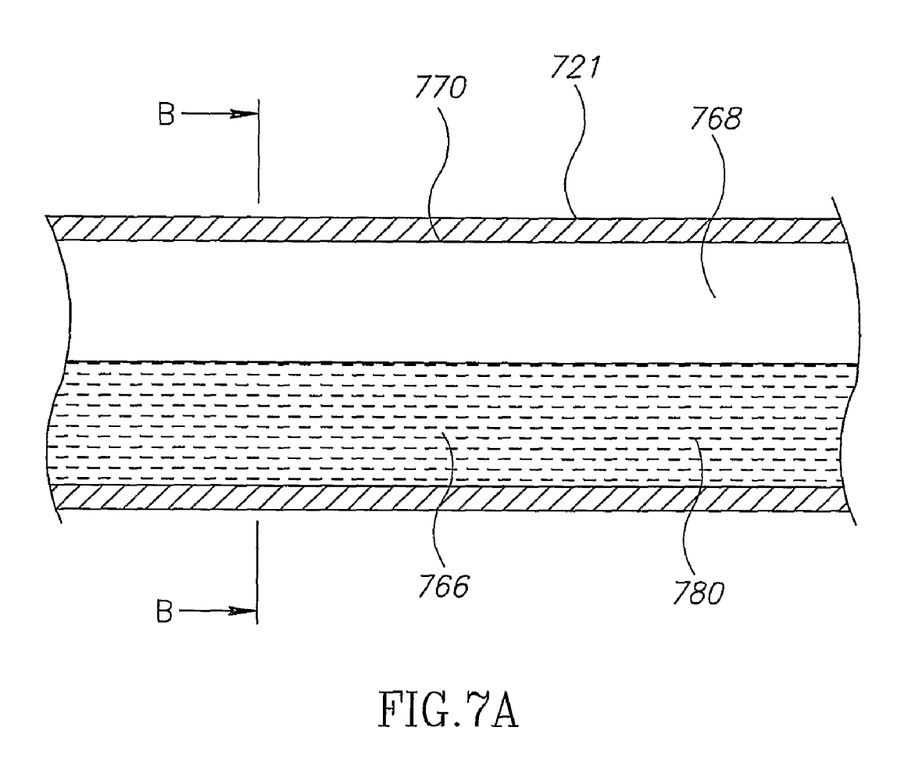
Figure 7B:
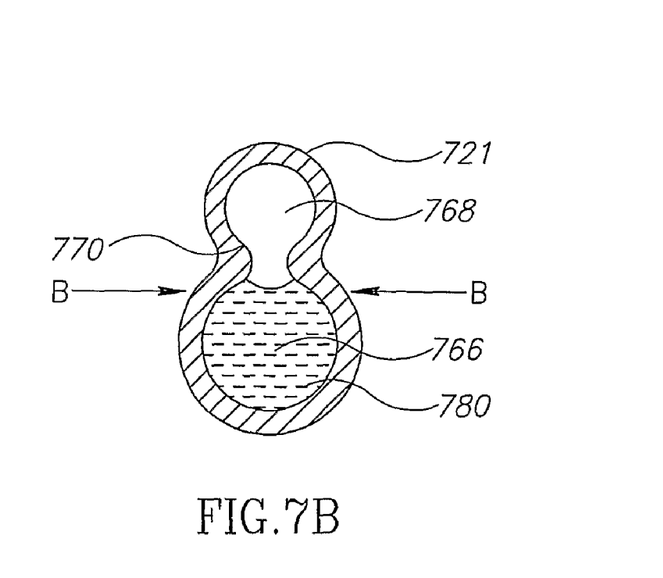

Reference is made to FIGS. 6a and 7a which show a longitudinal cross-sectional view of a portion of a sampling tube (621, 721) in two alternate embodiments of the sampling tube (621, 721), and FIGS. 6b and 7b, respectively, which show a transversal cross-sectional view B-B of a portion of the sampling tube (621, 721) in the two alternate embodiments of the sampling tube (621, 721). In these embodiments the sampling tube (621, 721) may include a hydrophobic material such that the liquids may be repelled out of the conduit (668, 768) by the effect of the hydrophobicity of the conduit wall (670, 770) and directed towards a tube collector (680, 780) for collected liquids (666, 766), which may be a part of the conduit (668, 768).

The sampling tube (621, 721) made be of a hydrophobic material, for example Teflon or polyacetal. Alternatively, the tube made not be of a hydrophobic material, for example PVC, and it may have a hydrophobic coating (not shown) installed along the conduit wall (670, 770) of the sampling tube (621, 721).

In FIGS. 6a and 6b the sampling tube (621) which may include a hydrophobic material and thus have a hydrophobic characteristics, may include a conduit (668) and a tube collector (680) which together are essentially shaped to resemble a "five petal flower". The cross section of the conduit (668) forms a "petal shaped" such that the conduit wall (670) basically extends between the "petals" into the mid-section of the "flower" which is essentially the tube collector (680). The liquids flowing in the conduit (668) are then repelled or pushed into the tube collector (680) as collected liquid (666), far away from the conduit (668). This then leaves the conduit (668) free for the passage of the exhaled breath sample.

In FIGS. 7a and 7b the sampling tube (721) which may include hydrophobic material and thus have a hydrophobic characteristics may include a conduit (768) and a tube collector (780) which together are essentially shaped to resemble the digit 8, the conduit (768) smaller in diameter than the tube collector (780). Due to the larger diameter of the tube collector (780), the liquid tends to flow from the conduit (768) to the tube collector (780) where it-accumulates as collected liquid (766), leaving the conduit (768) essentially free for the passage of the exhaled breath sample.

The preferred embodiment and the alternate embodiments shown in FIGS. 5a and 5b to 7a and 7b are for illustrative purposes only and are not intended to limit the possible shapes of the sampling tube to those illustrated. For hydrophilic materials and/or coatings all possible shapes which may provide a greater contact surface area between the conduit and the liquids and which do not interfere with the exhaled breath sample waveform may be acceptable. For hydrophobic materials and/or coatings all possible shapes which may provide a greater liquid repelling surface area between the conduit and the liquids and which do not interfere with the exhaled breath sample waveform may be acceptable.

What we claim is:

1. A breath sampling tube comprising: an inner conduit, wherein at least a portion of the inner conduit is non-cylindrical and adapted to store liquids, wherein the cross section of said inner conduit is substantially similar to an n-petal flower or an n-point star, wherein n is an integer having the value of between 2-10.

2. The tube according to claim 1, wherein said inner conduit is further adapted to permit gas flow out of said conduit wherein said gas is essentially free of liquids.

3. The tube according to claim 1, wherein said inner conduit is adapted to store liquids along the surface of said conduit and to permit gas flow along the central portion of said conduit.

4. The tube according to claim 1, wherein said inner conduit is adapted to permit gas flow along the surface of said conduit and to store liquids along the central portion of said conduit.

5. The tube according to claim 1, wherein the walls, of said inner conduit comprises a hydrophilic material.

6. The tube according to claim 1, wherein the walls of said inner conduit comprises a hydrophobic material.

7. The tube according to claim 1, wherein a portion of the walls of said inner conduit comprises a hydrophilic material and another portion of the walls of said inner conduit comprises a hydrophobic material.

8. The tube according to claim 1, wherein said inner conduit is adapted to permit self-drying of said liquids.

9. The tube according to claim 1, wherein said inner conduit is further adapted to permit gas flow out of said conduit wherein said gas is essentially free of liquids.

10. A breath sampling system comprising: a gas analyzer; and a breath sampling tube comprising an inner conduit, wherein at least a portion of said inner conduit is non-cylindrical and adapted to store liquids, wherein the cross section of said inner conduit is substantially similar to an n-petal flower or an n-point star, wherein n is an integer having the value of between 2-10.

11. The breath sampling system according to claim 10, wherein said inner conduit is adapted to store liquids along the surface of said conduit and to permit gas flow along the central portion of said conduit.

12. The breath sampling system according to claim 10, wherein said inner conduit is adapted to permit gas flow along the surface of said conduit and to store liquids along the central portion of said conduit.

13. The breath sampling system according to claim 10, wherein the walls, of said inner conduit comprises a hydrophilic material.

14. The breath sampling system according to claim 10, wherein the walls of said inner conduit comprises a hydrophobic material.

15. The breath sampling system according to claim 10, wherein a portion of the walls of said inner conduit comprises a hydrophilic material and another portion of the walls of said inner conduit comprises a hydrophobic material.

16. The breath sampling system according to claim 10, wherein said inner conduit is adapted to permit self-drying of said liquids.

17. A method of breath sampling comprising: channeling breath through a tube having an inner conduit, wherein at least a portion of said inner conduit is non-cylindrical and adapted to store liquids, wherein the cross section of said inner conduit is substantially similar to an n-petal flower or an n-point star, wherein n is an integer having the value of between 2-10.

18. The method according to claim 17, wherein said inner conduit is adapted to store liquids along the surface of said conduit and to permit gas flow along the central portion of said conduit.

19. The method according to claim 17, wherein said inner conduit is adapted to permit gas flow along the surface of said conduit and to store liquids along the central portion of said conduit.

20. The method according to claim 17, wherein the walls of said inner conduit comprises a hydrophilic material.

21. The method according to claim 17, wherein the walls of said inner conduit comprises a hydrophobic material.

22. The method according to claim 17, wherein a portion of the walls of said inner conduit comprises a hydrophilic material and another portion of the walls of said inner conduit comprises a hydrophobic material.

23. The method according to claim 17, wherein said inner conduit is adapted to permit self-drying of said liquids.

* * * * *